(12) United States Patent
Suh et al.

(10) Patent No.: US 9,834,489 B2
(45) Date of Patent: Dec. 5, 2017

(54) METHOD FOR PRODUCING BIO-AROMATICS FROM GLYCEROL

(71) Applicant: INDUSTRY-UNIVERSITY COOPERATION FOUNDATION HANYANG UNIVERSITY, Seoul (KR)

(72) Inventors: Young-Woong Suh, Seoul (KR); Hyung-Su Jang, Seoul (KR); Kyung-Bok Bae, Changwon-si (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 0 days.

(21) Appl. No.: 14/718,264

(22) Filed: May 21, 2015

(65) Prior Publication Data
US 2015/0336856 A1    Nov. 26, 2015

(30) Foreign Application Priority Data
May 21, 2014    (KR) .................. 10-2014-0060932

(51) Int. Cl.
| | | |
|---|---|---|
| *C07C 1/20* | (2006.01) | |
| *C07C 1/22* | (2006.01) | |
| *C07C 1/24* | (2006.01) | |
| *C10G 3/00* | (2006.01) | |
| *B01J 37/03* | (2006.01) | |
| *B01J 23/06* | (2006.01) | |
| *B01J 23/28* | (2006.01) | |
| *B01J 23/75* | (2006.01) | |
| *B01J 29/072* | (2006.01) | |
| *B01J 29/076* | (2006.01) | |
| *B01J 29/40* | (2006.01) | |
| *B01J 37/02* | (2006.01) | |

(52) U.S. Cl.
CPC .............. *C07C 1/20* (2013.01); *B01J 23/06* (2013.01); *B01J 23/28* (2013.01); *B01J 23/75* (2013.01); *B01J 29/072* (2013.01); *B01J 29/076* (2013.01); *B01J 29/40* (2013.01); *B01J 37/0201* (2013.01); *B01J 37/031* (2013.01); *C10G 3/46* (2013.01); *C10G 3/49* (2013.01); *C10G 3/52* (2013.01); *B01J 2229/12* (2013.01); *B01J 2229/38* (2013.01); *C07C 2529/40* (2013.01); *C07C 2529/46* (2013.01); *C07C 2529/48* (2013.01); *C10G 2300/1011* (2013.01); *C10G 2400/30* (2013.01); *Y02E 50/13* (2013.01); *Y02P 30/20* (2015.11)

(58) Field of Classification Search
CPC .................................... C07C 1/00; C07C 1/22
See application file for complete search history.

(56) References Cited

U.S. PATENT DOCUMENTS

| | | | |
|---|---|---|---|
| 8,207,385 B2* | 6/2012 | O'Connor ............. | C10G 11/18 208/113 |
| 2012/0203042 A1* | 8/2012 | Huber ................... | C10L 349/22 585/241 |
| 2014/0101988 A1* | 4/2014 | Feng ...................... | C10L 1/191 44/351 |

FOREIGN PATENT DOCUMENTS

CN    103357430 A    10/2013

OTHER PUBLICATIONS

Hoang et al., Conversion of glycerol to alkyl-aromatics over zeolites, Jun. 11, 2010, Energy and Fuels, vol. 24, pp. 3804-3809.*
Office Action dated Nov. 16, 2016 in Korean Patent Application No. 10-2014-0060932.
Sohrab Fathi et al., "Improvement of HZSM-5 performance by alkaline treatments: Comparative catalytic study in the MTG reactions", Fuel, 116 (2014) pp. 529-537.
Guanqun Luo, et al., "Conversion of Methanol and Glycerol into Gasoline via ZSM-5 Catalysis", Energy & Fuels, American Chemical Society, 2014, 28, pp. 600-606.

* cited by examiner

*Primary Examiner* — In Suk Bullock
*Assistant Examiner* — Youngsul Jeong
(74) *Attorney, Agent, or Firm* — Oblon, McClelland, Maier & Neustadt, L.L.P.

(57) ABSTRACT

Provided is a method for producing bio-aromatic compounds from glycerol. The method uses a primary alcohol, secondary alcohol or a combination thereof as a mixing medium in converting glycerol into an aromatic compound, and thus overcomes the high viscosity of glycerol and improves the problem of rapid catalytic deactivation, thereby increasing the yield of aromatic compounds and improving the stability of catalyst. In addition, the method for producing bio-aromatic compounds uses a zeolite-based catalyst that is a kind of solid acid catalysts, and suggests optimum reaction conditions, and thus imparts a high added value to glycerol produced as a byproduct in a biodiesel production process and increases the cost-efficiency of process.

6 Claims, No Drawings

METHOD FOR PRODUCING BIO-AROMATICS FROM GLYCEROL

CROSS-REFERENCE TO RELATED APPLICATIONS

This application claims priority under 35 U.S.C. §119 to Korean Patent Application No. 10-2014-0060932, filed on May 21, 2014, in the Korean Intellectual Property Office, the disclosure of which is incorporated herein by reference in its entirety.

TECHNICAL FIELD

The following disclosure relates to a method for producing bio-aromatic compounds from glycerol. More particularly, the following disclosure relates to a method for producing bio-aromatic compounds used as biofuel by carrying out reaction of a mixed charge containing glycerol mixed with a primary or secondary alcohol to reduce the high viscosity of glycerol over a zeolite-based solid acid catalyst.

BACKGROUND

Ecumenically, there is an increasing need for technological development about raw materials as petroleum alternative resources so as to cope with a continuous demand in basic petrochemical products such as light olefins and aromatics at high-oil price situation. Currently, at least 90% of aromatics based on the global demand have been produced through naphtha reforming processes of oil companies and naphtha cracking processes of petrochemical companies. Before 2005, efforts were concentrated in developing technologies, such as aromatic alkylation and transalkylation, capable of maximizing BTX (benzene, toluene, xylene) fractions among the existing aromatic products. On the other hand, since 2006, as the market environment of naphtha-based aromatic compound production changes, many studies have been conducted to develop novel and improved technologies for improving cost-efficiency.

However, it is expected that competitiveness derived from dependence on naphtha decreases, and thus aromatic production technology independent on naphtha may ensure competitiveness and easily enters the market. Therefore, advanced countries such as Europe, North America and Japan have conducted many studies to produce basic petrochemical products by utilizing petroleum alternative raw materials such as non-food biomass. Particularly, studies about bio-ethanol have been conducted most actively. Ethanol, which is a raw material that can be obtained easily from petroleum alternative resources, has been developed first among liquid biofuel and already used for transportation in Brazil or the like. Recently, active studies have been conducted for the production of ethanol from natural gas or non-food biomass. Under these circumstances, research and development on production technologies of basic chemicals based on ethanol has been conducted all over the world.

Meanwhile, among biomass resources, some studies have been conducted on the conversion of glycerol produced as a byproduct in a biodiesel production process into a high-added value compound. Particularly, most of such studies are for producing 1,2-propanediol, 1,3-propanediol, acrolein, etc., used as a solvent or basic chemical from glycerol. However, there are not many studies about production of aromatic compounds from glycerol. Recently, R. G. Mallinson, D. E. Resasco and coworkers of Oklahoma University (USA) have issued the results of their study about production of alkyl group-substituted aromatic compounds using zeolite (Energy & Fuels, 2010, Vol. 24, pp. 3804-3809). However, according to the results, it is reported that rapid deactivation of catalyst occurs to cause degradation of catalytic activity within a short time, and oxygen-containing compounds corresponding to intermediates are obtained with a higher yield as compared to aromatic compounds. As a result, there is a need for a means for increasing the yield of aromatic compounds.

REFERENCES (Non-patent Document 1) Trung Q. Hoang, Xinli Zhu, Tanate Danuthai, Lance L. Lobban, Daniel E. Resasco and Richard G. Mallinson, 'Conversion of Glycerol to Alkyl-aromatics over Zeolites', Energy & Fuels, 2010, Vol. 24, pp. 3804-3809

SUMMARY

An embodiment of the present disclosure is directed to improving the problems occurring in the processes for producing aromatic compounds from glycerol as a byproduct of a biodiesel production process according to the related art. More particularly, an embodiment of the present disclosure is directed to providing a method for producing bio-aromatic compounds from glycerol, wherein the method improves the problem of high viscosity (1.412 Pa·s) of glycerol to supply reaction materials smoothly for the aromatization of glycerol, provides optimized reaction conditions for producing aromatic compounds selectively rather than oxygen-containing compounds, and improves the problem of degradation of the life of a catalyst caused by rapid deactivation.

In one aspect, there is provided a method for producing bio-aromatic compounds, including a step of carrying out reaction of a mixed charge containing glycerol and an alcohol over a solid acid catalyst.

According to an embodiment, the alcohol may be a primary alcohol, secondary alcohol or a combination thereof. For example, the primary alcohol may be methanol or ethanol, and the secondary alcohol may be isopropanol or isobutanol.

According to another embodiment, the glycerol may be used in an amount of 5-50 wt % based on the total weight of mixed charge.

According to still another embodiment, the reaction of a mixed charge containing glycerol and an alcohol over a solid acid catalyst may be carried out at 400-450° C.

According to still another embodiment, the mixed charge may be supplied at a weight hourly space velocity of 0.5-4 $h^{-1}$.

According to still another embodiment, the method may further include a step of preheating the mixed charge and the preheating may be carried out at 300-400° C.

According to still another embodiment, the solid acid catalyst may be a zeolite-based catalyst.

According to still another embodiment, the zeolite-based catalyst may have a ratio of $SiO_2/Al_2O_3$ of 30-280 and may include pores expanded by sodium oxide (NaOH) or sodium carbonate ($Na_2CO_3$).

According to yet another embodiment, the zeolite-based catalyst may include at least one element selected from the group consisting of zinc, molybdenum, copper, manganese, potassium, titanium, chrome, cesium, lanthanum, silver, rhenium, zirconium and a combination thereof, and the element may be introduced in an amount of 0.5-20 wt % based on the total weight of catalyst.

The method for producing bio-aromatic compounds d according to the present disclosure uses a primary alcohol, secondary alcohol or a combination thereof as a mixing medium in converting glycerol into an aromatic compound, and thus overcomes the high viscosity of glycerol and improves the problem of rapid catalytic deactivation, thereby increasing the yield of aromatic compounds and improving the stability of catalyst. In addition, the method according to the present disclosure uses a zeolite-based catalyst that is a kind of solid acid catalysts, and suggests optimum reaction conditions, and thus provides a high-added value to glycerol produced as a byproduct in a biodiesel production process and increases the cost-efficiency of the process.

DETAILED DESCRIPTION OF EMBODIMENTS

Hereinafter, various aspects and exemplary embodiments of the present disclosure will be described in more detail.

Recently, active studies have been conducted about production of basic chemicals based on ethanol. In addition, among biomass resources, many studies have been conducted to convert glycerol produced as a byproduct during a biodiesel production process into a high-added value compound. Particularly, most of such studies are for producing 1,2-propanediol. 1,3-propanediol, acrolein, etc., used as a solvent or basic chemical from glycerol.

However, there are not many studies about production of aromatic compounds from glycerol. Recently, studies about production of alkyl group-substituted aromatic compounds using zeolite have been disclosed but they have problems in that the catalyst are deactivated rapidly and oxygen-containing compounds corresponding to intermediates are produced with a higher yield as compared to aromatic compounds.

Therefore, there is a need for a method for producing aromatic compounds which provides the reaction conditions optimized for producing aromatic compounds selectively rather than oxygen-containing compounds, improves the problem of degradation of catalyst life caused by rapid deactivation of catalyst and increases the yield of aromatic compounds.

In one aspect, there is provided a method for producing bio-aromatic compounds, including a step of carrying out reaction of a mixed charge containing glycerol and an alcohol over a solid acid catalyst.

According to an embodiment, a primary alcohol, secondary alcohol or a combination thereof may be used as a mixing medium to supply the reaction materials for aromatization smoothly by reducing the high viscosity of glycerol.

For example, the primary alcohol may be methanol or ethanol, and the secondary alcohol may be isopropanol or isobutanol, but is not limited thereto.

According to another embodiment, the glycerol may be used preferably in an amount of 5-50 wt % based on the total weight of mixed charge.

According to still another embodiment, the reaction of a mixed charge containing glycerol and an alcohol over a solid acid catalyst may be carried out at 400-450° C. When the temperature is lower than 400° C., there is a limitation in converting the supplied reaction materials into aromatic compounds. When the temperature is higher than 450° C., the supplied reaction materials may be converted into gaseous products, resulting in a drop in the yield of aromatic compounds.

The mixed charge containing glycerol and an alcohol according to the present disclosure may be supplied preferably at a weight hourly space velocity (WHSV) of 0.5-5 $h^{-1}$, and more preferably at a WHSV of 0.5-4 $h^{-1}$. When the weight hourly space velocity is less than 0.5 $h^{-1}$, the necessary amount of catalyst increases as compared to the amount of raw materials to be treated, resulting in degradation of cost-efficiency. When the weight hourly space velocity is higher than 5 $h^{-1}$, the conversion of mixed charge decreases.

The method according to the present disclosure may further include a step of preheating the mixed charge containing glycerol and an alcohol prior to the step of carrying out reaction of the mixed charge containing glycerol and an alcohol over a sold acid catalyst in order to prevent droplet formation of glycerol, to transfer the charge along with nitrogen and to make the temperature higher than the boiling point (290° C.) of glycerol. Herein, the preheating may be carried out by maintaining the internal temperature of a fluid pipe of mixed charge at 300-400° C.

In addition, the method according to the present disclosure may further include a step of condensing the vapor phase flow passing through a reactor during the step of carrying out reaction of the mixed charge containing glycerol and an alcohol over a sold acid catalyst into a liquid, and collecting aromatic compounds. Herein, one condenser or at least two condensers connected successively may be used to condense the vapor phase flow including the reaction product after reaction. Particularly, the condenser is maintained preferably at a temperature of −10 to 10° C. When the temperature of condenser is lower than −10° C., aromatic compounds may be solidified to block the fluid pipe. When the temperature of condenser is higher than 10° C., not all the aromatic compounds are condensed, resulting in loss of the yield.

In the method according to the present disclosure, the solid acid catalyst may be a zeolite-based catalyst. Generally, zeolite is prepared from the hydrothermal reaction of an alkaline silica-alumina mixture and is used as an adsorbent and catalyst in various applications. Particularly, zeolite is used widely as a solid acid catalyst by virtue of: 1) a broad surface area provided by micropores, 2) thermal stability and hydrothermal stability provided by its very regular crystal structure, 3) shape selectivity depending on pore size, 4) acid strength and acidity controllability of aluminum ions forming zeolite. Particularly, zeolite has been used widely in various reactions, including cracking, isomerization, alkylation and catalytic reforming.

In the zeolite-based catalyst according to the present disclosure, the ratio of $SiO_2/Al_2O_3$ is a main factor determining the acidity of catalyst and the zeolite-based catalyst preferably has a broad range of ratio of 30-280 and more preferably 30-80. When the molar ratio is less than 30, deactivation of catalyst occurs rapidly. When the ratio is more than 280, it is not possible to provide sufficient acidity, resulting in a drop of the yield of bio-aromatic compounds.

Particularly, the zeolite-based catalyst according to the present disclosure may be protonated HZSM-5 catalyst but is not limited thereto.

The zeolite-based catalyst according to the present disclosure may have pores expanded by sodium oxide (NaOH) or sodium carbonate ($Na_2CO_3$).

Herein, since HZSM-5 catalyst used according to an embodiment is converted into Na-ZSM-5 catalyst, it is further converted into $NH_4$-ZSM-5 catalyst by using ammonium nitrate and then heat treated in a hot firing furnace. Finally, HZSM-5 catalyst having expanded pores is provided and used for reaction. However, preparation of a catalyst is not limited to the above-described method, which may be modified partially by those skilled in the art.

According to an embodiment, the zeolite-based catalyst may include at least one element selected from the group consisting of zinc, molybdenum, copper, manganese, potassium, titanium, chrome, cesium, lanthanum, silver, rhenium, zirconium and a combination thereof, and the element may be introduced in an amount of 0.5-20 wt % based on the total weight of the catalyst.

Introduction of the element may be carried out by an impregnation method and precipitation method. The impregnation method includes dissolving a metal precursor into distilled water of the volume corresponding to the pore volume of HZSM-5 catalyst that is a matrix used according to an embodiment, and impregnating the matrix with the aqueous solution to obtain a catalyst. The precipitation method includes introducing the matrix into distilled water to prepare suspension and supporting a metal in the matrix by introducing aqueous solution containing a metal precursor dissolved therein and solution of a precipitating agent simultaneously to the suspension in a predetermined amount to obtain a catalyst. However, preparation of a catalyst is not limited to the above-described impregnation method and precipitation method, which may be modified partially by those skilled in the art.

According to the method for producing bio-aromatic compounds of the present disclosure, it is possible to increase the yield of aromatic compounds to at most 60% based on the carbon mole number of mixed charge introduced to the reaction by means of the continuous dehydration and condensation of mixed charge containing glycerol and an alcohol over the catalyst layer. Herein, the proportion of benzene, toluene and xylene may be approximately 75% based on resultant aromatic compounds obtained by the above-described method.

The examples and experiments will now be described. The following examples and experiments are for illustrative purposes only and not intended to limit the scope of this disclosure.

COMPARATIVE EXAMPLE 1

Experiment of Aromatization Using Aqueous Glycerol Solution

First, glycerol is provided in an amount of 25-70 wt % based on the total weight of aqueous glycerol solution. When the aqueous glycerol solution is supplied as reactant, the reaction conditions are as follows: a temperature of 440-550° C., weight hourly space velocity (WHSV) of 0.8 $h^{-1}$, and HZSM-5 zeolite having a $SiO_2/Al_2O_3$ ratio of 30, as a catalyst. The following Table 1 shows the distribution and total yield of aromatic compounds obtained from the experiments carried out different conditions.

TABLE 1

Results of Aromatization of Aqueous Glycerol Solution Depending on Glycerol Content and Reaction Temperature

| | | Reaction temperature | | Yield of products (%) | | | | | | | Total yield of aromatic |
|---|---|---|---|---|---|---|---|---|---|---|---|
| No. | Content | (° C.) | WHSV | Benzene | Toluene | Xylene | Ethylbenzene | C9 aromatics | C10 aromatics | C11 Aromatics | compounds |
| 1 | 25% | 440° C. | 0.8 $h^{-1}$ | 1.19 | 4.51 | 14.64 | 0.87 | 6.70 | 1.66 | 5.41 | 34.99 |
| 2 | 30% | 440° C. | 0.8 $h^{-1}$ | 0.82 | 4.61 | 11.70 | 0.74 | 4.77 | 1.13 | 2.47 | 26.25 |
| 3 | 36% | 440° C. | 0.8 $h^{-1}$ | 1.16 | 4.97 | 10.97 | 0.66 | 5.93 | 1.29 | 2.45 | 27.43 |
| 4 | 46% | 440° C. | 0.8 $h^{-1}$ | 0.89 | 5.12 | 11.20 | 0.81 | 4.34 | 1.18 | 1.74 | 25.29 |
| 5 | 70% | 440° C. | 1.0 $h^{-1}$ | 1.35 | 6.54 | 9.82 | 0.72 | 3.98 | 0.89 | 1.11 | 24.42 |
| 6 | 30% | 400° C. | 0.8 $h^{-1}$ | 0.56 | 1.68 | 6.19 | 0.53 | 4.76 | 1.06 | 2.49 | 17.27 |
| 7 | 30% | 480° C. | 0.8 $h^{-1}$ | 0.69 | 4.82 | 10.89 | 0.89 | 4.12 | 1.53 | 2.70 | 25.63 |
| 8 | 30% | 500° C. | 0.8 $h^{-1}$ | 0.82 | 4.64 | 10.41 | 0.88 | 3.46 | 1.32 | 2.41 | 23.94 |

As can be seen from the above results, the main product of mixed charge containing glycerol and water is xylene. As the content of glycerol increases, the total yield of aromatic compounds and xylene selectivity increase and catalyst deactivation decreases. When the reaction temperature is changed, the yield of aromatic compounds and catalytic activity decrease significantly at a reaction temperature of 400° C. as compared to the other reaction temperatures. At 500° C., the yield of aromatic compounds decreases significantly as compared to 400° C. but the duration of catalytic activity increases. As a result, it can be seen that use of mixed charge containing glycerol and water provides the total yield of aromatic compounds corresponding to about 30%. In addition, it is observed that the catalyst is deactivated with the lapse of reaction time, suggesting that there is a need for improvement.

COMPARATIVE EXAMPLE 2

Experiment of Aromatization of Aqueous Glycerol Solution Using Metal-Supported HZSM-5 Catalyst In this example, a metal is supported in the catalyst used according to Comparative Example 1 in order to increase the total yield of aromatic compounds. Metals used herein include zinc, gallium and copper, which are supported in HZSM-5 catalyst having a $SiO_2/Al_2O_3$ ratio of 30 through an impregnation method. The thus prepared catalyst is used to carry out aromatization of aqueous glycerol solution and the results are shown in the following Table 2. The reaction is carried out at a temperature of 480° C. with a WHSV of 0.8 $h^{-1}$. The concentration of glycerol in aqueous glycerol solution is 30 wt % based on the total weight of aqueous glycerol solution introduced as reactant.

TABLE 2

Results of Aromatization of Aqueous Glycerol Solution Using Metal-Supported Catalyst

| No. | Type of metal | Reaction temperature (° C.) | WHSV | Yield of products (%) | | | | | | | Total yield of aromatic compounds |
| --- | --- | --- | --- | --- | --- | --- | --- | --- | --- | --- | --- |
| | | | | Benzene | Toluene | Xylene | Ethylbenzene | C9 aromatics | C10 aromatics | C11 aromatics | |
| 9 | Zn | 480° C. | 0.8 h$^{-1}$ | 1.2 | 5.42 | 13.53 | 0.63 | 2.48 | 0.61 | 2.84 | 26.71 |
| 10 | Ga | 480° C. | 0.8 h$^{-1}$ | 1.26 | 4.86 | 14.41 | 0.89 | 4.85 | 1.33 | 2.95 | 30.65 |
| 11 | Cu | 480° C. | 0.8 h$^{-1}$ | 1.15 | 5.14 | 18.74 | 0.89 | 4.69 | 0.83 | 2.49 | 33.92 |

It can be seen from the above results that when comparing the metal-supported catalysts with the matrix HZSM-5 (SiO$_2$/Al$_2$O$_3$=30) catalyst, the total yield of aromatic compounds slightly increases and the xylene selectivity slightly varies with the particular type of metal. Thus, it is shown that the effect of metal supported in HZSM-5 catalyst upon the reaction for producing aromatic compounds from aqueous glycerol solution is not significant.

EXAMPLE 1

Experiment of Aromatization Using Glycerol/Methanol

Mixed Charge (1) Methanol is mixed with glycerol and supplied as reactant in order to reduce the viscosity of glycerol and contribute to formation of aromatic compounds along with glycerol. Glycerol is provided in an amount of 10.7-48.9 wt % based on the total weight of mixed charge. The reaction conditions are as follows: a temperature of 400° C., WHSV of 0.8 h$^{-1}$, and HZSM-5 zeolite having a SiO$_2$/Al$_2$O$_3$ ratio of 30, as a catalyst. The following Table 3 shows the distribution and total yield of aromatic compounds obtained by using glycerol/methanol mixed charge having a different part by weight of methanol.

As can be seen from Table 3, use of mixed charge containing 19.3 wt % of glycerol provides the highest yield of aromatic compounds and shows a reaction stability corresponding to 35% of aromatic compounds up to 38 hours. When glycerol content is 10.7 wt %, the yield of aromatic compounds is maintained for 43.6 hours. In addition, 19.3 wt % of glycerol content corresponds to 35.6 hours, 25 wt % corresponds to 12 hours, 32.4 wt % corresponds to 7.3 hours, and 48.9 wt % corresponds to 4.5 hours. In other words, as the glycerol content increases, reaction stability gradually decreases.

It can be seen from the above results that the glycerol/methanol mixed charge provides significant improvement in the yield of aromatic compounds and catalytic activity duration as compared to aqueous glycerol solution as a reaction charge. In addition, the main product is xylene, followed by trimethylbenzene. Among the three isomers of xylene, meta-xylene occupies 50% of total xylene, and para-xylene and ortho-xylene occupy 26% and 24%, respectively. In the case of trimethylbenzene, 1,2,4-trimethylbenzene occupies 90% of total trimethylbenzene, and 1,3,5-trimethylbenzene and 1,2,3-trimethylbenzene occupy 6.5% and 3.5%, respectively. However, the yield of trimethylbenzene increases gradually as the reaction proceeds. As a result, the main product is changed from xylene into trimethylbenzene. Such a trend appears in all experiments using a glycerol/methanol mixed charge.

(2) To improve the yield of aromatic compounds, reaction temperature of reaction variables is varied and experiments of aromatization of a glycerol/methanol mixed charge are

TABLE 3

Results of Aromatization of Glycerol/Methanol Mixed Charge Depending on Glycerol Content

| No. | Content | Reaction temperature (° C.) | WHSV | Yield of products (%) | | | | | | | Total yield of aromatic compounds |
| --- | --- | --- | --- | --- | --- | --- | --- | --- | --- | --- | --- |
| | | | | Benzene | Toluene | Xylene | Ethylbenzene | C9 aromatics | C10 aromatics | C11 aromatics | |
| 12 | 10.7% | 400° C. | 0.8 h$^{-1}$ | 0.3 | 2.5 | 16.4 | 0.3 | 18.32 | 0.05 | 0.51 | 38.48 |
| 13 | 19.3% | 400° C. | 0.8 h$^{-1}$ | 0.59 | 5.39 | 20.07 | 0.62 | 17.49 | 0.08 | 0.80 | 45.04 |
| 14 | 25.0% | 400° C. | 0.8 h$^{-1}$ | 0.4 | 3.4 | 17.2 | 0.5 | 17.47 | 0.10 | 0.77 | 39.84 |
| 15 | 32.4% | 400° C. | 0.8 h$^{-1}$ | 0.31 | 2.69 | 14.8 | 0.38 | 14.85 | 0.20 | 1.11 | 34.34 |
| 16 | 48.9% | 400° C. | 0.8 h$^{-1}$ | 0.39 | 2.81 | 15.0 | 0.37 | 14.33 | 0.29 | 1.71 | 35.30 | carried out. The glycerol content used herein is 19.3 wt % where the highest yield of aromatic compounds is provided, and WHSV is 0.8 h$^{-1}$. The catalyst used herein is HZSM-5 having a SiO$_2$/Al$_2$O$_3$ ratio of 30 as shown in Table 3. Experiments are carried out while varying the reaction temperature within a range of 370 to 480° C.

TABLE 4

Results of Aromatization of Glycerol/Methanol Mixed Charge Depending on Reaction Temperature

| | | Reaction | | Yield of products (%) | | | | | | | Total yield of |
|---|---|---|---|---|---|---|---|---|---|---|---|
| No. | Content | temperature (° C.) | WHSV | Benzene | Toluene | Xylene | Ethylbenzene | C9 aromatics | C10 aromatics | C11 aromatics | aromatic compounds |
| 17 | 19.3% | 370° C. | 0.8 h$^{-1}$ | 0.49 | 6.42 | 18.83 | 0.67 | 12.82 | 0.11 | 1.47 | 40.81 |
| 13 | 19.3% | 400° C. | 0.8 h$^{-1}$ | 0.59 | 5.39 | 20.07 | 0.62 | 17.49 | 0.08 | 0.80 | 45.04 |
| 18 | 19.3% | 420° C. | 0.8 h$^{-1}$ | 0.87 | 7.94 | 20.23 | 0.60 | 15.20 | 0.09 | 0.82 | 45.75 |
| 19 | 19.3% | 440° C. | 0.8 h$^{-1}$ | 0.89 | 7.93 | 18.36 | 0.55 | 12.07 | 0.08 | 0.70 | 40.58 |
| 20 | 19.3% | 480° C. | 0.8 h$^{-1}$ | 0.63 | 6.22 | 14.59 | 0.49 | 9.68 | 0.09 | 0.60 | 32.32 |

As can be seen from Table 4, at a reaction temperature of 400-420° C., the highest yield of aromatic compounds is provided and a relatively long catalytic activity duration is provided as compared to the other reaction temperatures. When carrying out aromatization by using a mixture of glycerol with water, a reaction temperature of 480° C. shows the highest yield. However, when using a glycerol/methanol mixed charge, a range of reaction temperatures lower than 480° C. provides the optimum yield. It is thought that this is because methanol and water used for mixing with glycerol have a different boiling point and methanol requires lower energy to participate in the reaction.

(3) The effect of catalyst contact time of the reaction variables in the aromatization using a glycerol/methanol mixed charge is determined. Experiments are carried out while varying weight hourly space velocity within a range of 0.5 to 4 h$^{-1}$. The glycerol content is 19.3 wt % and reaction temperature is 400° C. The catalyst used herein is HZSM-5 having a SiO$_2$/Al$_2$O$_3$ ratio of 30.

TABLE 5

Results of Aromatization of Glycerol/Methanol Mixed Charge Depending on Weight Hourly Space Velocity (WHSV)

| | | Reaction | | Yield of products (%) | | | | | | | Total yield of |
|---|---|---|---|---|---|---|---|---|---|---|---|
| No. | Content | temperature (° C.) | WHSV | Benzene | Toluene | Xylene | Ethylbenzene | C9 aromatics | C10 aromatics | C11 aromatics | aromatic compounds |
| 21 | 19.3% | 400 | 0.5 h$^{-1}$ | 0.76 | 7.62 | 18.91 | 0.45 | 12.50 | 0.16 | 1.71 | 42.12 |
| 13 | 19.3% | 400 | 0.8 h$^{-1}$ | 0.59 | 5.39 | 20.07 | 0.62 | 17.49 | 0.08 | 0.80 | 45.04 |
| 22 | 19.3% | 400 | 2 h$^{-1}$ | 1.01 | 8.85 | 18.98 | 0.44 | 11.26 | 0.14 | 1.23 | 41.92 |
| 23 | 19.3% | 400 | 4 h$^{-1}$ | 0.70 | 6.38 | 19.63 | 0.66 | 11.65 | 0.09 | 0.79 | 39.89 |

As can be seen from Table 5, a weight hourly space velocity of 0.8 h$^{-1}$ shows the highest yield of aromatic compounds. In the experiments of conversion of a glycerol/methanol mixed charge into aromatic compounds, the highest yield of aromatic compounds is obtained when the glycerol content is 19.3 wt %, reaction temperature is 400° C. and weight hourly space velocity is 0.8 h$^{-1}$.

(4) The reaction is carried out for 38 hours under the above-mentioned conditions to observe variations in aromatic compound products depending on time. The results are shown in Table 6. The yield of aromatic compounds starts from 28% at the initial time of reaction, reaches the highest yield of 45.0%, gradually decreases, and maintains 32.38% even at 38 hours, the end of reaction. As the reaction time increases, selectivity to C9 aromatic compounds increases, resulting in a change in main product from xylene to C9 aromatic compounds. Herein, about 80% of aromatic compounds is occupied by trimethylbenzene.

TABLE 6

Results of Aromatization of Glycerol/Methanol Mixed Charge Depending on Reaction Time

| | | Reaction | | Yield of products (%) | | | | | | | Total yield of |
|---|---|---|---|---|---|---|---|---|---|---|---|
| No. | Reaction time | temperature (° C.) | WHSV | Benzene | Toluene | Xylene | Ethylbenzene | C9 aromatics | C10 aromatics | C11 aromatics | aromatic compounds |
| 24 | 3.0 | 400° C. | 0.8 h$^{-1}$ | 0.83 | 6.32 | 12.67 | 0.53 | 7.53 | 0.12 | 0.70 | 28.70 |
| 13 | 12.0 | 400° C. | 0.8 h$^{-1}$ | 0.59 | 5.39 | 20.07 | 0.62 | 17.49 | 0.08 | 0.80 | 45.04 |
| 25 | 20.2 | 400° C. | 0.8 h$^{-1}$ | 0.31 | 3.24 | 17.73 | 0.53 | 19.42 | 0.05 | 0.59 | 41.87 |

TABLE 6-continued

Results of Aromatization of Glycerol/Methanol Mixed Charge Depending on Reaction Time

| No. | Reaction time | Reaction temperature (° C.) | WHSV | Yield of products (%) | | | | | | | Total yield of aromatic compounds |
| --- | --- | --- | --- | --- | --- | --- | --- | --- | --- | --- | --- |
| | | | | Benzene | Toluene | Xylene | Ethylbenzene | C9 aromatics | C10 aromatics | C11 aromatics | |
| 26 | 24.9 | 400° C. | 0.8 h$^{-1}$ | 0.25 | 2.61 | 17.93 | 0.53 | 22.77 | 0.05 | 0.58 | 44.72 |
| 27 | 31.6 | 400° C. | 0.8 h$^{-1}$ | 0.20 | 2.05 | 15.25 | 0.47 | 20.29 | 0.03 | 0.36 | 38.64 |
| 28 | 38.1 | 400° C. | 0.8 h$^{-1}$ | 0.15 | 1.47 | 12.42 | 0.37 | 17.69 | 0.02 | 0.24 | 32.38 |

EXAMPLE 2

Experiment of Aromatization Using Glycerol/Ethanol Mixed Charge

Ethanol is mixed with glycerol instead of methanol used in Example 1 and supplied as reactant. Glycerol is provided in an amount of 14.3-40.0 wt % based on the total weight of mixed charge. The reaction conditions are as follows: a temperature of 400° C., WHSV of 0.8 h$^{-1}$, and HZSM-5 zeolite having a SiO$_2$/Al$_2$O$_3$ ratio of 30, as a catalyst. The following Table 7 shows the distribution and total yield of aromatic compounds obtained by using a glycerol/ethanol mixed charge depending on glycerol content.

TABLE 7

Results of Aromatization of Glycerol/Ethanol Mixed Charge Depending on Glycerol Content

| No. | Content | Reaction temperature (° C.) | WHSV | Yield of products (%) | | | | | | | Total yield of aromatic compounds |
| --- | --- | --- | --- | --- | --- | --- | --- | --- | --- | --- | --- |
| | | | | Benzene | Toluene | Ethylbenzene | | C9 aromatics | C10 aromatics | C11 aromatics | |
| 29 | 14.3% | 400° C. | 0.8 h$^{-1}$ | 2.67 | 12.59 | 11.91 | 1.75 | 6.46 | 0.36 | 1.40 | 37.15 |
| 30 | 18.2% | 400° C. | 0.8 h$^{-1}$ | 2.68 | 12.57 | 11.85 | 1.79 | 6.15 | 0.34 | 1.43 | 36.80 |
| 31 | 25% | 400° C. | 0.8 h$^{-1}$ | 2.59 | 11.79 | 11.48 | 1.72 | 6.03 | 0.37 | 1.31 | 35.30 |
| 32 | 40% | 400° C. | 0.8 h$^{-1}$ | 2.87 | 11.64 | 10.77 | 1.53 | 5.51 | 0.71 | 2.41 | 35.45 |

As can be seen from Table 7, unlike aqueous glycerol solution and the glycerol/methanol mixed charge, the glycerol/ethanol mixed charge provides toluene as a main product instead of xylene. In addition, unlike the glycerol/methanol mixed charge, the proportion of ethyltoluene in the resultant C9 aromatic compounds is about 50% and the production of C10 aromatic compounds and C11 aromatic compounds increases. In brief, it can be seen that when the glycerol/ethanol mixed charge has a glycerol content of 14.3 wt %, the highest yield of aromatic compounds is provided.

EXAMPLE 3

Experiment of Aromatization Using Glycerol/Isopropanol Mixed Charge and Glycerol/Isobutanol Mixed Charge A secondary alcohol (isopropanol, isobutanol) is mixed with glycerol instead of the primary alcohols used in Examples 1 and 2, and supplied as reactant. The glycerol/isopropanol mixed charge contains glycerol in an amount of 11.3-25 wt % and the glycerol/isobutanol mixed charge contains glycerol in an amount of 9.4-25 wt %. The reaction conditions are as follows: a temperature of 400° C., WHSV of 0.8 h$^{-1}$, and HZSM-5 zeolite having a SiO$_2$/Al$_2$O$_3$ ratio of 30, as a catalyst. The following Tables 8 and 9 show the distribution and total yield of aromatic compounds obtained by using the glycerol/isopropanol mixed charge and glycerol/isobutanol mixed charge, respectively.

TABLE 8

Results of Aromatization of Glycerol/Isopropanol Mixed Charge Depending on Glycerol Content

| No. | Content | Reaction temperature (° C.) | WHSV | Benzene | Toluene | Xylene | Ethylbenzene | C9 aromatics | C10 aromatics | C11 aromatics | Total yield of aromatic compounds |
|---|---|---|---|---|---|---|---|---|---|---|---|
| 33 | 11.3% | 400° C. | 0.8 h$^{-1}$ | 3.70 | 14.20 | 11.24 | 1.47 | 4.48 | 0.43 | 1.29 | 36.83 |
| 34 | 25% | 400° C. | 0.8 h$^{-1}$ | 3.03 | 13.80 | 13.07 | 1.82 | 6.46 | 0.41 | 1.57 | 40.16 |

TABLE 9

Results of Aromatization of Glycerol/Isobutanol Mixed Charge Depending on Glycerol Content

| No. | Content | Reaction temperature (° C.) | WHSV | Benzene | Toluene | Xylene | Ethylbenzene | C9 aromatics | C10 aromatics | C11 aromatics | Total yield of aromatic compounds |
|---|---|---|---|---|---|---|---|---|---|---|---|
| 35 | 9.4% | 400° C. | 0.8 h$^{-1}$ | 4.46 | 16.21 | 12.30 | 1.42 | 4.41 | 0.81 | 3.27 | 42.89 |
| 36 | 25% | 400° C. | 0.8 h$^{-1}$ | 3.32 | 13.20 | 12.21 | 1.59 | 5.68 | 0.49 | 1.93 | 38.42 |

As can be seen from Tables 8 and 9, similarly to the results of reaction using a glycerol/ethanol mixed charge, it is observed that the main product is toluene and the yield of xylene increases as the glycerol content increases. In addition, the main ingredients of C9-C11 aromatic compounds are ethyltoluene and naphthalene. In the case of a glycerol/isopropanol mixed charge, the yield of aromatic compounds is 40% when the glycerol content is 25 wt %. In the case of a glycerol/isobutanol mixed charge, the yield of aromatic compounds is 42.9% when the glycerol content is 9.4 wt %.

EXAMPLE 4

Experiment of Aromatization Using Glycerol/Methanol Mixed Charge Depending on SiO$_2$/Al$_2$O$_3$ Ratio of HZSM-5 Catalyst In this example, effects of SiO$_2$/Al$_2$O$_3$ ratio of HZSM-5 catalyst upon the aromatization using a glycerol/methanol mixed charge are determined. Herein, the ratio of SiO$_2$/Al$_2$O$_3$ is 30. The reaction conditions are as follows: a temperature of 400° C., WHSV of 0.8 h$^{-1}$, and a glycerol content of 19.3 wt %. The following Table 10 shows the distribution and total yield of aromatic compounds obtained by using a glycerol/methanol mixed charge in the presence of HZSM-5 catalysts having a different SiO$_2$/Al$_2$O$_3$ ratio.

When the SiO$_2$/Al$_2$O$_3$ ratio of HZSM-5 catalyst is 30, aromatization of the glycerol/methanol mixed charge shows the highest yield of aromatics. In addition, HZSM-5 catalyst having a ratio of SiO$_2$/Al$_2$O$_3$ of 30 shows reduced deactivation and provides excellent results in terms of reaction stability.

EXAMPLE 5

Experiment of Aromatization Using Glycerol/Methanol Mixed Charge Depending on Pore Size of HZSM-5 Catalyst In this example, the pore size of HZSM-5 catalyst is expanded to increase the duration of catalytic activity and to determine the distribution of aromatic compounds. To expand the pore size, an alkaline material (NaOH, Na$_2$CO$_3$) is used to carry out silica removal by extracting silica (SiO$_2$) forming the zeolite. The HZSM-5 catalyst used herein has a SiO$_2$/Al$_2$O$_3$ ratio of 30. The following Table 11 shows the distribution and total yield of aromatic compounds obtained from a glycerol/methanol mixed charge in the presence of HZSM-5 catalyst having pores expanded by using an alkaline material. The reaction conditions are the same as the reaction conditions of Example 4.

TABLE 10

Results of Aromatization of Glycerol/Methanol Mixed Charge Depending on SiO$_2$/Al$_2$O$_3$ Ratio of HZSM-5 Catalyst

| No. | SiO$_2$/Al$_2$O$_3$ ratio | Reaction temperature (° C.) | WHSV | Benzene | Toluene | Xylene | Ethylbenzene | C9 aromatics | C10 aromatics | C11 aromatics | Total yield of aromatic compounds |
|---|---|---|---|---|---|---|---|---|---|---|---|
| 13 | 30 | 400° C. | 0.8 h$^{-1}$ | 0.59 | 5.39 | 20.07 | 0.62 | 17.49 | 0.08 | 0.80 | 45.04 |
| 37 | 80 | 400° C. | 0.8 h$^{-1}$ | 0.94 | 7.21 | 17.34 | 0.77 | 12.24 | 0.20 | 1.10 | 40.21 |
| 38 | 280 | 400° C. | 0.8 h$^{-1}$ | 0.21 | 2.30 | 12.18 | 0.68 | 10.46 | 0.03 | 0.20 | 26.27 |

TABLE 11

Results of Aromatization of Glycerol/Methanol Mixed Charge Using HZSM-5 Catalyst Having Expanded Pores

| No. | Material for removing silica | Reaction temperature (° C.) | WHSV | Benzene | Toluene | Xylene | Ethylbenzene | C9 aromatics | C10 aromatics | C11 Aromatic | Total yield of aromatic compounds |
|---|---|---|---|---|---|---|---|---|---|---|---|
| 13 | Parent | 400 | 0.8 h$^{-1}$ | 0.59 | 5.39 | 20.07 | 0.62 | 17.49 | 0.08 | 0.80 | 45.04 |
| 39 | 0.1M NaOH | 400 | 0.8 h$^{-1}$ | 1.57 | 10.91 | 18.87 | 0.70 | 9.02 | 0.17 | 0.93 | 42.17 |
| 40 | 0.5M NaOH | 400 | 0.8 h$^{-1}$ | 1.57 | 10.19 | 18.06 | 0.76 | 9.54 | 0.18 | 1.05 | 41.36 |
| 41 | 0.5M Na$_2$CO$_3$ | 400 | 0.8 h$^{-1}$ | 1.44 | 9.72 | 16.10 | 0.43 | 6.61 | 0.20 | 0.98 | 35.48 |

First, silica-removed Na-ZSM-5 catalyst is provided by agitating HZSM-5 catalyst (SiO$_2$/Al$_2$O$_3$=30) with aqueous NaOH or Na$_2$CO$_3$ solution having a concentration of 0.1-0.5M at 80° C. for 1 hour. Then, the catalyst is further agitated with 1M aqueous ammonium nitrate solution at 80° C. for 3 hours so that it may be converted into NH$_4$-ZSM-5 catalyst. Finally, the resultant catalyst is fired in a firing furnace at 600° C. for 3 hours to obtain silica-removed HZSM-5 catalyst. After analyzing the pore size distribution by nitrogen adsorption/desorption analysis, it is shown that mesopores are formed, which suggests that the pores of HZSM-5 catalyst are expanded.

As can be seen from Table 11, when compared with non-treated HZSM-5 catalyst, the highest yield of aromatic compounds slightly decreases in the case of the silica-removed HZSM-5 catalyst but deactivation of catalyst proceeds more rapidly than deactivation of the matrix catalyst. Although such pore size expansion of HZSM-5 catalyst has no significant effect upon the aromatization of a glycerol/methanol mixed charge, it is expected that optimization of pore size increases the yield of aromatic compounds.

EXAMPLE 6

Experiment of Aromatization of Glycerol/Methanol Mixed Charge Using Metal-Supported Zeolite Catalyst Obtained by Impregnation Method In this example, the effect of metal supported in HZSM-5 catalyst upon the aromatization using a glycerol/methanol mixed charge is observed. Metals used herein include Zn, Mo and Cu and HZSM-5 catalyst has a SiO$_2$/Al$_2$O$_3$ ratio of 30. In addition, an impregnation method is used to introduce a metal, and the amount of metal supported in the catalyst is set to 1 wt % to compare metal activities with each other. Metal-supported HZSM-5 catalyst is reduced with 50 cc/min of hydrogen at 480° C. for 2 hours. The following Table 12 shows the distribution and total yield of aromatic compounds obtained from a glycerol/methanol mixed charge in the presence of HZSM-5 catalysts having different metals supported therein. The reaction conditions are the same as the reaction conditions of Example 4.

TABLE 12

Results of Aromatization of Glycerol/Methanol Mixed Charge Using Metal-Supported Catalyst Obtained by Impregnation Method

| No. | Metal type | Reaction temperature (° C.) | WHSV | Benzene | Toluene | Xylene | Ethylbenzene | C9 aromatics | C10 aromatics | C11 aromatics | Total yield of aromatic compounds |
|---|---|---|---|---|---|---|---|---|---|---|---|
| 13 | Parent | 400° C. | 0.8 h$^{-1}$ | 0.59 | 5.39 | 20.07 | 0.62 | 17.49 | 0.08 | 0.80 | 45.04 |
| 42 | 1 wt % Zn | 400° C. | 0.8 h$^{-1}$ | 0.9 | 10.1 | 25.9 | 0.9 | 16.94 | 0.10 | 1.02 | 55.8 |
| 43 | 1 wt % Mo | 400° C. | 0.8 h$^{-1}$ | 0.97 | 8.13 | 20.31 | 0.86 | 14.11 | 0.12 | 0.94 | 45.44 |
| 44 | 1 wt % Cu | 400° C. | 0.8 h$^{-1}$ | 0.37 | 3.66 | 14.69 | 0.56 | 14.93 | 0.13 | 0.92 | 35.26 |

As can be seen from Table 12, when using Zn-supported HZSM-5 catalyst, the yield of aromatic compounds is 55.8%. However, duration of catalytic activity is reduced as compared to the matrix catalyst (non-metal supported HZSM-5). In addition, it can be seen from the distribution of aromatic compounds produced from a glycerol/methanol mixed charge by using Zn- or Cu-supported HZSM-5 catalyst that production of toluene, ethylbenzene, C10 aromatics (naphthalene) and C11 aromatics (methyl naphthalene) is increased slightly.

EXAMPLE 7

Experiment of Aromatization of Glycerol/Methanol Mixed Charge Using Zn-Supported Zeolite Catalyst Obtained by Impregnation Method In this example, aromatization of a glycerol/methanol mixed charge is carried out by using a different amount of Zn to determine the activity of a Zn-supported zeolite that shows the highest activity in Example 6. The following Table 13 shows the distribution and total yield of aromatic compounds obtained from a glycerol/methanol mixed charge in the presence of Zn-supported HZSM-5 catalyst. To support Zn in HZSM-5 (SiO$_2$/Al$_2$O$_3$=30) catalyst, an impregnation method is used in the same manner as Example 6. The reaction conditions are the same as the reaction conditions of Example 4.

TABLE 13

Results of Aromatization of Glycerol/Methanol Mixed Charge Depending on Amount of Zn Supported by Impregnation Method

| No. | Wt ratio of Zn | Reaction temperature (° C.) | WHSV | Benzene | Toluene | Xylene | Ethylbenzene | C9 aromatics | C10 aromatics | C11 aromatics | Total yield of aromatic compounds |
|---|---|---|---|---|---|---|---|---|---|---|---|
| 42 | 1% | 400° C. | 0.8 h$^{-1}$ | 0.9 | 10.1 | 25.9 | 0.9 | 16.94 | 0.10 | 1.02 | 55.8 |
| 45 | 2% | 400° C. | 0.8 h$^{-1}$ | 0.8 | 10.3 | 25.2 | 0.9 | 16.73 | 0.12 | 0.34 | 54.4 |
| 46 | 4% | 400° C. | 0.8 h$^{-1}$ | 0.3 | 4.6 | 24.0 | 0.8 | 23.46 | 0.05 | 0.58 | 53.8 |
| 47 | 9% | 400° C. | 0.8 h$^{-1}$ | 0.2 | 4.4 | 21.7 | 1.1 | 16.62 | 0.00 | 0.33 | 44.3 |

As can be seen from Table 13, when using Zn-supported HZSM-5 catalysts having a different Zn content of 1-9 wt % in the aromatization of a glycerol/methanol mixed charge, the yield of aromatic compounds gradually decreases as the Zn content increases. Accordingly, duration of catalytic activity decreases. To determine variations in catalyst property depending on increase in Zn content, ammonia temperature-programmed desorption analysis and nitrogen adsorption/desorption analysis are carried out. After the analysis, it is shown that strong acid points decrease and surface area gradually decreases as Zn content increases. As a result, it is thought that optimization of Zn content supported in the catalyst can maximize the yield of aromatic compounds.

EXAMPLE 8

Experiment of Aromatization of Glycerol/Methanol Mixed Charge Using Zn-Supported Zeolite Catalyst Obtained by Precipitation Method Zinc is introduced to HZSM-5 catalyst through a precipitation method instead of the impregnation method used in Example 7. This is because a precipitation method enables a larger amount of zinc to be supported in the catalyst. Thus, a catalyst obtained by supporting 2.0-19.2 wt % of zinc in HZSM-5 (SiO$_2$/Al$_2$O$_3$=30) catalyst is used to carry out the aromatization of a glycerol/methanol mixed charge. The reaction conditions are the same as the reaction conditions of Example 4.

ethylbenzene) decreases. However, similarly to the catalyst having Zn supported therein through an impregnation method, duration of catalytic activity is lower as compared to the matrix catalyst, and gradually decreases as the amount of zinc metal increases.

What is claimed is:

1. A method for producing bio-aromatic compounds, the method comprising:
   conducting a reaction by reacting a mixed charge comprising glycerol and an alcohol in the presence of a HZSM-5 zeolite catalyst having a SiO$_2$/Al$_2$O$_3$ ratio of 30 to 80, at a temperature of 400 to 420° C. and a weight hourly space velocity of 0.5 to 2 h$^{-1}$, to produce a product mixture comprising at least one bio-aromatic compound formed from the glycerol and the alcohol; and
   recovering the product mixture,
   wherein the alcohol is selected from the group consisting of methanol, ethanol, isopropanol, isobutanol, with the proviso that the amount of glycerol in the mixed charge is (i) in a range of 19.3 to 25 wt % when the alcohol is methanol, (ii) in a range of 14.3 to 25 wt % when the alcohol is ethanol, (iii) in a range of 11.3 to 25 wt % when the alcohol is isopropanol, or (iv) in a range of 9.4 to 25 wt % when the alcohol is isobutanol.

2. The method according to claim 1, further comprising:
   preheating the mixed charge.

TABLE 14

Results of Aromatization of Glycerol/Methanol Mixed Charge Depending on Amount of Zn Supported by Precipitation Method

| No. | Wt ratio of Zn | Reaction temperature (° C.) | WHSV | Benzene | Toluene | Xylene | Ethylbenzene | C9 aromatics | C10 aromatics | C11 aromatics | Total yield of aromatic compounds |
|---|---|---|---|---|---|---|---|---|---|---|---|
| 13 | Parent | 400 | 0.8 h$^{-1}$ | 0.59 | 5.39 | 20.07 | 0.62 | 17.49 | 0.08 | 0.80 | 45.04 |
| 48 | 2 wt % Zn | 400 | 0.8 h$^{-1}$ | 1.23 | 12.41 | 24.50 | 0.49 | 13.09 | 0.22 | 1.13 | 53.06 |
| 49 | 9 wt % Zn | 400 | 0.8 h$^{-1}$ | 1.15 | 12.55 | 22.56 | 0.85 | 11.63 | 0.15 | 0.75 | 49.65 |
| 50 | 19.2 wt % Zn | 400 | 0.8 h$^{-1}$ | 1.23 | 12.44 | 23.50 | 0.76 | 14.08 | 0.13 | 0.73 | 52.87 |

As can be seen from Table 14, in the case of HZSM-5 catalyst having Zn supported therein by a precipitation method, the yield of aromatic compounds increases by about 4-8% as compared to the matrix catalyst (non-metal supported HZSM-5 (SiO$_2$/Al$_2$O$_3$=30)). Referring to the distribution of aromatic compound products, in the case of Zn-supported catalysts, production of toluene, ethylbenzene, C10 aromatics and C11 aromatics increase as compared to the matrix catalyst, while production of C9 aromatics (trim- 3. The method according to claim 1, further comprising:
   subjecting the HZSM-5 zeolite catalyst to desilication to produce a desilicated HZSM-5 zeoltie catalyst by expanding its pores with sodium hydroxide (NaOH) or sodium carbonate (Na$_2$CO$_3$) prior to the reaction,
   wherein the amount of mesopores in the desilicated HZSM-5 zeolite catalyst is more than that in the pre-desilicated HZSM-5 zeolite catalyst.

4. The method according to claim 1, wherein:
the HZSM-5 zeolite catalyst comprises at least one metal element selected from the group consisting of zinc, molybdenum, copper, manganese, potassium, titanium, chromium, cesium, lanthanum, silver, rhenium and zirconium;
the at least one metal element is supported on the HZSM-5 zeolite catalyst in its reduced form; and
the amount of the at least one metal element is in a range of 0.5 to 20 wt % based on a total weight of the HZSM-5 zeolite catalyst.

5. The method according to claim 4, wherein the metal element is zinc, the amount of zinc being in a range of up to 1 wt % based on a total weight of the HZSM-5 zeolite catalyst.

6. The method according to claim 1, further comprising:
condensing a vapor phase flow comprising the reaction product after the reaction, and collecting the at least one bio-aromatic compound therefrom,
wherein the condensing is carried out using a condenser or at least two condensers connected successively to each other, the condenser being maintained at a temperature of −10 to 10° C.

* * * * *